(12) United States Patent
Van Dorpe et al.

(10) Patent No.: US 8,867,032 B2
(45) Date of Patent: Oct. 21, 2014

(54) SURFACE ENHANCED OPTICAL DETECTION SUBSTRATE FOR SENSING PURPOSES AND METHODS FOR MANUFACTURING

(75) Inventors: Pol Van Dorpe, Spalbeek (BE); Kristof Lodewijks, Lommel (BE); Masahiko Shioi, Osaka (JP); Jian Ye, Leuven (BE)

(73) Assignees: IMEC, Leuven (BE); Panasonic Corporation, Osaka (JP); Katholieke Universiteit Leuven, Ku Leuven R&D, Leuven (BE)

( * ) Notice: Subject to any disclaimer, the term of this patent is extended or adjusted under 35 U.S.C. 154(b) by 108 days.

(21) Appl. No.: 13/634,620

(22) PCT Filed: Mar. 22, 2011

(86) PCT No.: PCT/EP2011/054381
§ 371 (c)(1),
(2), (4) Date: Sep. 13, 2012

(87) PCT Pub. No.: WO2011/117260
PCT Pub. Date: Sep. 29, 2011

(65) Prior Publication Data
US 2013/0003058 A1 Jan. 3, 2013

(30) Foreign Application Priority Data

Mar. 22, 2010 (EP) ..................................... 10157261
Mar. 23, 2010 (EP) ..................................... 10157445

(51) Int. Cl.
*G01J 3/44* (2006.01)
*B82Y 30/00* (2011.01)
(Continued)

(52) U.S. Cl.
CPC ............ *G01N 21/658* (2013.01); *G01N 21/648* (2013.01); *G01N 21/554* (2013.01); *G01N 21/553* (2013.01); *B82Y 30/00* (2013.01); *B82Y 15/00* (2013.01); *B22F 2001/0029* (2013.01); *Y10S 977/773* (2013.01)
USPC .......................................... 356/301; 977/773

(58) Field of Classification Search
CPC ... G01N 21/658; G01N 21/65; G01N 21/648; G01N 27/3271; G01N 21/553; G01N 21/554; G01J 3/44; B82Y 15/00; B82Y 30/00; B22F 2001/0029
USPC ........................................... 356/301; 977/773
See application file for complete search history.

(56) References Cited

U.S. PATENT DOCUMENTS 6,274,293 B1 * 8/2001 Gupta et al. ................... 430/315
7,046,358 B2 * 5/2006 Barker et al. ................. 356/301
(Continued)

OTHER PUBLICATIONS

Aizpurua, J. et al., "Optical Properties of Gold Nanorings," The American Physical Society, Physical Review Letters, Feb. 7, 2003, vol. 90, No. 5, pp. 057401-1 through 057401-4.
(Continued)

*Primary Examiner* — Kara E Geisel
*Assistant Examiner* — Violeta A Prieto
(74) *Attorney, Agent, or Firm* — McDonnell Boehnen Hulbert & Berghoff LLP

(57) ABSTRACT

A substrate is described that is suitable for surface enhanced optical detection. The substrate comprises an electrically conductive layer The substrate further comprises at least one nanoparticle comprising an electrically conductive portion. The electrically conductive portion may provide an opening to an underlying material. Such at least one nanoparticles may be a nanoring, a nanodisc, or a non-spherical nanoshell. The substrate further comprises a dielectric spacer for spacing the electrically conductive layer from the at least one nanoparticles. The dielectric spacer is a dielectric material substantially only present under the at least one nanoparticle, leaving the electrically conductive layer uncovered from dielectric material at positions away from the nanoparticles. The at least one nanoparticle and the dielectric spacer are interfaced along a first major surface and the at least one nanoparticle comprises an upstanding surface not in line with an upstanding surface of the dielectric spacer.

12 Claims, 12 Drawing Sheets

(51) Int. Cl.
  *B82Y 15/00*  (2011.01)
  *G01N 21/65*  (2006.01)
  *G01N 21/64*  (2006.01)
  *G01N 21/55*  (2014.01)
  *B22F 1/00*  (2006.01)

(56) References Cited

U.S. PATENT DOCUMENTS

| | | | |
|---|---|---|---|
| 7,359,048 B2* | 4/2008 | Wang et al. | 356/301 |
| 7,639,354 B2* | 12/2009 | Wang et al. | 356/301 |
| 8,149,397 B2* | 4/2012 | Lee et al. | 356/301 |
| 8,568,878 B2* | 10/2013 | Wilson et al. | 428/402 |
| 2006/0056463 A1* | 3/2006 | Wang et al. | 372/3 |
| 2007/0252982 A1 | 11/2007 | Wang et al. | |
| 2009/0213369 A1* | 8/2009 | Lee et al. | 356/301 |
| 2010/0323173 A1* | 12/2010 | Van Roy et al. | 428/208 |
| 2011/0116089 A1* | 5/2011 | Schmidt et al. | 356/301 |
| 2012/0057163 A1* | 3/2012 | Cheng et al. | 356/445 |
| 2012/0105857 A1* | 5/2012 | Lee et al. | 356/445 |
| 2013/0028840 A1* | 1/2013 | Van Roy et al. | 424/9.1 |
| 2013/0115413 A1* | 5/2013 | Eres et al. | 428/120 |
| 2014/0002824 A1* | 1/2014 | Cheng et al. | 356/440 |
| 2014/0104606 A1* | 4/2014 | Shih | 356/301 |

OTHER PUBLICATIONS

Banaee et al., "Gold nanorings as substrates for surface-enhanced Raman scattering," Optic Letters, Mar. 1, 2010, vol. 35, No. 5, pp. 760-762.

Bechelany, M. et al., "Extended domains of organized nanorings of silver grains as surface-enhanced Raman scattering senors for molecular detections," Nanotechnology, Nov. 11, 2009, vol. 20, No. 45, pp. 1-8.

Hao, Feng et al., "Shedding light on dark plasmons in gold nanorings," Chemical Physical Letters, 2008, vol. 458, pp. 262-266.

International Searching Authority, Written Opinion for PCT/EP2011/054381 mailed Jun. 15, 2011, 7 pages.

International Searching Authority, International Preliminary Report on Patentability for PCT/EP2011/054381 dated May 16, 2012, 14 pages.

International Search Report for PCT/EP2011/054381 mailed Jun. 15, 2011, 3 pages.

Prikulis et al., "Optical Spectroscopy of Nanometric Holes in Thin Gold Films," Nano Letters, Jun. 2004, vol. 4, No. 6, pp. 1003-1007.

Ye, Jian et al., "Observation of plasmonic dipolar anti-bonding mode in silver nanoring structures," Nanotechnology, 2009, vol. 20, pp. 1-6.

* cited by examiner

SURFACE ENHANCED OPTICAL DETECTION SUBSTRATE FOR SENSING PURPOSES AND METHODS FOR MANUFACTURING

CROSS REFERENCE TO RELATED APPLICATIONS

The present application is a national stage entry of PCT/EP2011/054381, filed Mar. 22, 2011, and claims priority to EP 10157261.8, filed Mar. 22, 2010, and EP 10157445.7, filed Mar. 23, 2010. The full disclosures of EP 10157261.8, EP 10157445.7, and PCT/EP2011/054381 are incorporated herein by reference.

FIELD OF THE INVENTION

The invention relates to the field of sensing. More particularly, the present invention relates to substrates for sensing via surface enhanced optical detection, methods of manufacturing them and methods and systems of using such substrates.

BACKGROUND OF THE INVENTION

Gold (Au) nano shells are nanoparticles usually composed of a dielectric core, typically silica, coated with an ultrathin Au layer. These nanoparticles show interesting optical and chemical properties for the applications of surface-enhanced Raman spectroscopy (SERS) sensor, surface plasmon resonance (SPR) sensor, drug delivery, biomedical imaging and cancer therapeutics among others.

Reducing symmetry of Au nanoshells geometry shows interesting properties. It is possible to excite different plasmon modes in these particles when compared to standard particles. These particles show angle dependent plasmon resonance. This unique property may lead to a new class of optically active nanoparticles that can be manipulated by applied static or frequency dependent electric, magnetic, or optical fields. The particles enhance the electric field intensity coming out of the particles when compared to fully covered particles, i.e. particles whose symmetry has not been reduced.

Several groups have developed and demonstrated reduced-symmetrical nanoshells such as nano half-shells, nanocups, nanomoons and nanoeggs for SERS applications. Reduced-symmetrical nanoshells have been prepared before in various ways including electron-beam evaporation (EBE) and electroless plating. By these methods, the reduced-symmetrical structures of nanoshells, such as nano aperture or nanotip, are usually oriented randomly or with their aperture downward, which obviously limits the molecular binding to the electric field enhanced regions in SERS applications. The Raman enhancement factors differ from place to place on a substrate because of the random orientation of reduced-symmetrical structures.

In "Observation of plasmonic dipolar anti-bonding mode in silver nanoring structures", Nanotechnology 20 (2009) 465203, Ye et al. explore plasmonic properties of silver and gold nanoring structures. It has been shown that reasonable SERS enhancement factors at near-infrared wavelengths can be achieved. Nevertheless, for a significant number of applications, the enhancement factor still is not high enough. Furthermore, for applications that do not involve single molecule measurements but aim at concentration determination, the enhancement factor integrated over the entire substrate is more relevant than the maximum enhancement factor. For the nanorings, the positions where high electric fields are reached are limited to the top edges of the nanorings, thus limiting the total interaction volume between the radiation and the molecules and thus limiting the integrated enhancement factor. There is still need for efficient Surface Enhanced Raman Scattering based sensing substrates.

SUMMARY OF THE INVENTION

It is an object of embodiments of the present invention to provide good surface enhanced optical detection substrates for sensing purposes, as well as methods of manufacturing them and methods and systems of using such substrates. It is an advantage of at least some embodiments according to the present invention that a high electromagnetic field enhancement factor can be reached, i.e. sufficiently high for most applications envisaged.

It is an advantage of at least some embodiments according to the present invention that the integrated enhancement factor can be good, i.e. that a good enhancement factor can be reached for a significant large interaction volume between the radiation and the substances to be measured.

It is an advantage of at least some embodiments according to the present invention that substrates with the above mentioned good enhancement factor and/or the above mentioned good integrated enhancement factor can be obtained in a reproducible way.

It is an advantage of embodiments according to the present invention that the substrates can be used for in vivo applications.

The above objective is accomplished by a method and device according to the present invention.

The present invention relates to a substrate for surface enhanced optical detection, the substrate comprising an electrically conductive layer, at least one nanoparticle comprising an electrically conductive portion, and a dielectric spacer for spacing the electrically conductive layer from the at least one nanoparticle, wherein the dielectric spacer is a dielectric material substantially only present under the at least one nanoparticle, leaving the electrically conductive layer uncovered from dielectric material at positions away from the nanoparticles, and wherein the at least one nanoparticle and the dielectric spacer are interfaced along a first major surface and wherein the at least one nanoparticle comprises an upstanding surface not in line with an upstanding surface of the dielectric spacer. The at least one nanoparticle may be at least one nanoring. The dielectric spacer may be a dielectric nanoring positioned under the at least one nanoparticle.

The at least one nanoparticle may be a nanodisc.

The dielectric spacer may be a dielectric disc positioned under the at least one nanoparticle.

A diameter of the dielectric spacer may be adapted for leaving a bottom side of the nanoparticle facing the electrically conductive layer partially uncovered.

The nanoparticles, dielectric spacer and electrically conductive layer may be arranged for having a quadrupolar charge distribution in the substrate.

The electrically conductive layer may be partially patterned, such that it comprises a top part being only locally present under the dielectric spacer and a bottom part being a continuous film.

The substrate may be integrated in a sensing device for sensing based on surface enhanced optical detection.

The sensing device may be adapted for sensing glucose.

The electrically conductive layer may be any of a gold, silver or aluminum layer.

The present invention also relates to a method for manufacturing a substrate suitable for surface enhanced optical detection, the method comprising
obtaining a supporting substrate
providing an electrically conductive layer on the supporting substrate,
providing a dielectric spacer layer on the electrically conductive layer,
providing at least one nanoparticle on the dielectric spacer layer, and removing the dielectric spacer layer at those positions where the dielectric spacer material is not positioned under the at least one nanoparticle such that the at least one nanoparticle and the dielectric spacer are interfaced along a first major surface and the nanoparticle comprises an upstanding surface not in line with an upstanding surface of the dielectric spacer.

Removing the dielectric spacer material may comprise etching the dielectric spacer material at those positions where the dielectric spacer is not positioned under the at least one nanoparticle.

The method furthermore may comprise partially patterning the electrically conductive layer for generating a top portion of the electrically conductive layer being only locally present under the dielectric spacer and a bottom portion of the electrically conductive layer being a continuous film.

The present invention also relates to a method comprising using a substrate for surface enhanced optical detection, the substrate comprising an electrically conductive layer, at least one nanoparticle comprising an electrically conductive portion, and a dielectric spacer for spacing the metal layer from the at least one nanoparticle wherein the dielectric spacer is a dielectric material substantially only present under the at least one nanoparticle, leaving the electrically conductive layer uncovered from dielectric material at positions away from the nanoparticles, and wherein the at least one nanoparticle and the dielectric spacer are interfaced along a first major surface and wherein the at least one nanoparticle comprises an upstanding surface not in line with an upstanding surface of the dielectric spacer.

The present invention in one aspect relates to a substrate for surface enhanced optical detection, the substrate comprising an electrically conductive layer, at least one nanoparticle comprising an electrically conductive portion, and a dielectric spacer for spacing the electrically conductive layer from the at least one nanoparticle, wherein the dielectric spacer is a dielectric material substantially only present under the at least one nanoparticle, leaving the electrically conductive layer uncovered from dielectric material at positions away from the nanoparticles, and wherein the electrically conductive layer may be partially patterned, such that it comprises a top part being only locally present under the dielectric spacer and a bottom part being a continuous film.

The present invention also relates to a method for manufacturing a substrate suitable for surface enhanced optical detection, the method comprising
obtaining a supporting substrate
providing an electrically conductive layer on the supporting substrate,
providing a dielectric spacer layer on the electrically conductive layer,
providing at least one nanoparticle on the dielectric spacer layer, and removing the dielectric spacer layer at those positions where the dielectric spacer material is not positioned under the at least one nanoparticle, and
partially patterning the electrically conductive layer for generating a top portion of the electrically conductive layer being only locally present under the dielectric spacer and a bottom portion of the electrically conductive layer being a continuous film.

The present invention relates to a substrate for surface enhanced optical detection, the substrate comprising an electrically conductive layer, at least one nanoparticle comprising an electrically conductive portion, and a dielectric spacer for spacing the electrically conductive layer from the at least one nanoparticle. It is an advantage of at least some embodiments of the present invention that a good enhancement factor for SERS is obtained with the substrates provided. It is an advantage of at least some embodiments of the present invention that such a good enhancement factor can be obtained for a substantially large volume of the nanoparticles, resulting in a good integrated enhancement factor. The nanoparticle may be an open nanoparticle, wherein the electrically conductive portion of the nanoparticle may provide an opening to an underlying material.

The open nanoparticle may be any of a non-spherical nanoshell or nanoring.

The dielectric spacer may be a dielectric material substantially only present under the at least one nanoparticles, leaving the electrically conductive layer uncovered by dielectric material at positions where no nanoparticles are present. It is an advantage of embodiments according to the present invention that the spacer can be positioned such that the metal layer itself, separately from interaction with the particles, also can contribute substantially to the enhancement factor.

The dielectric spacer may be a dielectric layer covering the electrically conductive layer. It is an advantage of embodiments according to the present invention that the spacer and electrically conductive layer can be easily made.

The at least one nanoparticle may be at least one nanoring. It is an advantage of embodiments according to the present invention that the combination of a nanoring and an electrically conductive layer results in areas of high electric fields being not limited to the edges of the nanoring.

The dielectric spacer may be a dielectric nanoring positioned under the nanoparticles. It is an advantage of at least some embodiments of the present invention that a spacer that prevents electrical contact between the nanoparticles and the electrically conductive layer without covering the full electrically conductive layer can easily be made.

The at least one nanoparticle may be at least one non-spherical nanoshell, the non-spherical nanoshell comprising a dielectric core partially surrounded by the electrically conductive portion, the uncovered part of the dielectric core being located at a side essentially opposite to the electrically conductive layer. It is an advantage of at least some embodiments according to the present invention that substrates can be obtained based on different types of nanoparticles, i.e. not only nanorings but e.g. also non-spherical-symmetric nanoshells.

The nanoparticles, dielectric spacer and electrically conductive portion may be arranged for having a quadrupolar charge distribution in the substrate. It is an advantage of at least some embodiments according to the present invention that a quadrupolar charge distribution results in a magnetic resonance, reducing strongly radiative scattering of the nanostructure, thus resulting in the reduction of losses. In this way, higher quality factors and more optical energy can be confined in the nanostructure.

The substrate may be integrated in a sensing device for sensing based on surface enhanced optical detection. It is an advantage of at least some embodiments according to the present invention that good sensing devices with high sensitivity can be obtained.

The sensing device may be adapted for sensing glucose. It is an advantage of at least some embodiments according to the present invention that an efficient glucose sensor can be obtained.

The electrically conductive layer may be any of a gold, silver or aluminum layer.

The present invention also relates to a method for manufacturing a substrate suitable for surface enhanced optical detection, the method comprising obtaining a supporting substrate, providing an electrically conductive layer on the supporting substrate, providing a dielectric spacer layer on the electrically conductive layer, providing at least one nanoparticle on the dielectric spacer layer, the at least one nanoparticle comprising an electrically conductive portion, the electrically conductive portion optionally providing an opening to an underlying material. It is an advantage of at least some embodiments according to the present invention that conventional processing steps can be used for manufacturing the different components of the substrate.

The method furthermore may comprise removing the dielectric spacer layer at those positions where the dielectric spacer is not positioned under the at least one nanoparticle.

Removing the dielectric spacer may comprise etching the dielectric spacer at those positions where the dielectric spacer is not positioned under the at least one nanoparticle.

The present invention also relates to a method of performing surface enhanced optical detection, the method comprising using a substrate for surface enhanced optical detection, the substrate comprising an electrically conductive layer, at least one nanoparticle comprising an electrically conductive portion, the electrically conductive portion optionally providing an opening to an underlying material, and a dielectric spacer for spacing the metal layer from the at least one nanoparticle.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
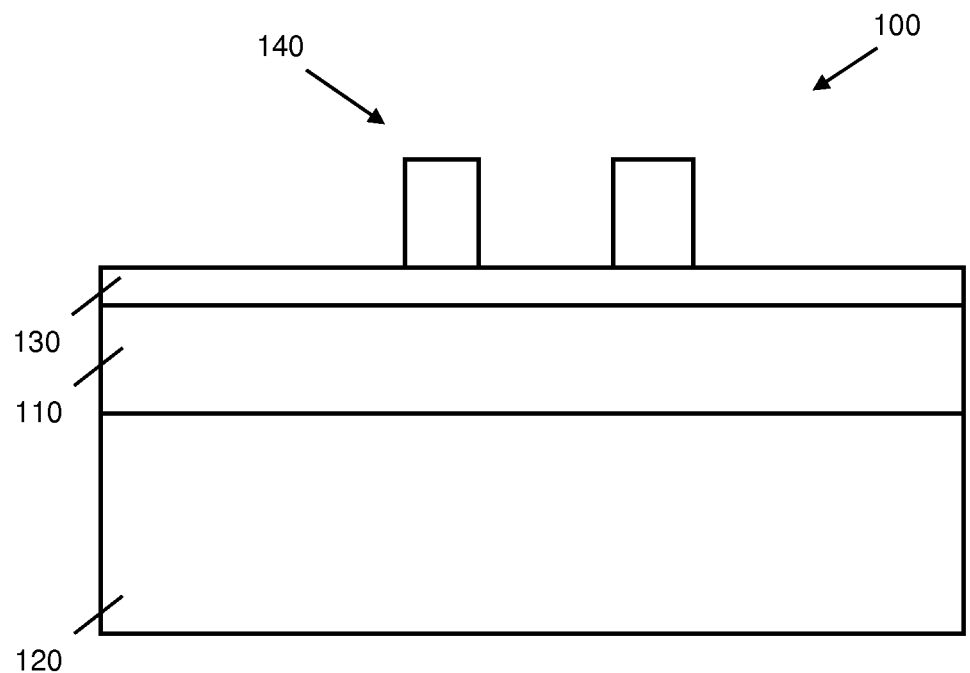
FIG. 1 illustrates a schematic representation of part of a substrate suitable for surface enhanced optical detection comprising a nanoring and metallic layer, according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

Where in embodiments of the present invention reference is made to "nanoparticle" reference is made to all types of nanoparticles such as for example open nanoparticles, spherical nanoparticles, nanodisks, etc.

Where in embodiments of the present invention reference is made to nano features, reference is made to nanopores, nano holes, nanoparticles, etc.

As used herein and unless stated otherwise, the term "open nanoparticles" relates to a nano particle being a nanoring or an open nanoshell or open shell nanoparticle. An open nanoshell or open shell nanoparticle refers to a nanoparticle with a dielectric core and non-complete or partial electrically conductive layer around the core. A nanoring or nanoring particle is a nanostructure having a ring or toroidal shape. An open nanoshell may be a non-spherical symmetrical portion of a nanosphere.

As used herein and unless stated otherwise, the term "nano" is used for referring to objects having typical characteristic lengths between 1 nm and 2000 nm, advantageously between 1 nm and 1000 nm.

Where in embodiments according to the present invention reference is made to a dielectric material being at positions away from the nanoparticles, reference is made to the presence of dielectric material under the nanoparticles. Where in embodiments according to the present invention reference is made to "under the nanoparticle", reference is made to a position under the electrically conductive portion of the nanoparticle or to a region enclosed thereby.

The invention will now be described by a detailed description of several embodiments of the invention. It is clear that other embodiments of the invention can be configured according to the knowledge of persons skilled in the art without departing from the technical teaching of the invention, the invention being limited only by the terms of the appended claims.

In a first aspect, the present invention relates to a substrate suitable for surface enhanced optical detection, such as for example surface enhanced Raman spectroscopy (SERS), based sensing. The substrate comprises an electrically conductive layer, at least one nanoparticle and a spacer separating the at least one nanoparticle from the electrically conductive layer. According to embodiments of the present invention, the dielectric spacer is a dielectric material substantially only being present under the at least one nanoparticle, leaving the electrically conductive layer uncovered from dielectric material at positions away from the nanoparticles. The at least one nanoparticle may be at least one open nanoparticle. The at least one open nanoparticle may comprise an electrically conductive portion whereby the electrically conductive portion is providing an opening to an underlying material. The open nanoparticle thus may for example be a nanoring or an open nanoshell. The at least one nanoparticle also may be a nanodisc supported by a dielectric nanodisc with smaller diameter. The substrates advantageously provide a high enhancement factor for surface enhanced optical detection. By way of illustration, embodiments of the present invention not being limited thereto, a more detailed description of features and advantages of at least some embodiments of the present invention will be described with respect to a representation of an exemplary substrate as shown in FIG. 1.

The substrate 100 suitable for surface enhanced optical detection based sensing comprises an electrically conductive layer 110 that may be positioned on a supporting layer or base substrate 120. Such a supporting layer may be made of any suitable material. The substrate may be any material, also conductive. It may for example comprise metal, dielectric or semi-conducting materials. Examples of metals suitable for the substrate comprise but are not limited to Ti, Cu, Al, Au, Ag. Examples of dielectric materials suitable for the substrate comprise but are not limited to glass, quartz, mica, $Si_3N_4$, $Al_2O_3$ and polymers among others. Examples of semi-conducting materials suitable for the substrate comprise but are not limited to Si, Ge, GaAs, group IV semi-conducting materials, group III-V semi-conducting materials, group II-VI semi-conducting materials and chalcopyrite among others. In embodiments, the substrate may be a planar substrate, a curved substrate or any other surface shape. Preferably, the substrate comprises a planar surface.

The electrically conducting layer 110 may be made of a metallic material (such as gold (Au), silver (Ag), nickel (Ni), titanium (Ti), aluminum (Al), copper (Cu) or platinum (Pt) amongst others), a semi-metallic material, or a (preferably doped) semiconducting material (such as Si or GaAs amongst others) or any other conducting material used in the field. Preferred conductive materials are metals and doped semiconductors. More preferably, the conductive material is a metal. The electrically conductive layer 110 can be made of a single conducting material or can comprise different conducting materials, for example selected from the list above. In some preferred embodiments, the electrically conductive layer 110 comprises at least on material selected from the group consisting of Au, Ag and Al. Most preferably, the electrically conductive layer 110 is made of gold. Electrically conductive layers 110 of various thickness are suitable. The thickness of the electrically conductive layer 110 can for example be from 20 nm to 200 nm, from 25 nm to 100 nm or from 30 nm to 50 nm. The thickness should be thick enough to support surface plasmons (i.e. at least as thick as the skin depth).

Figure 2:
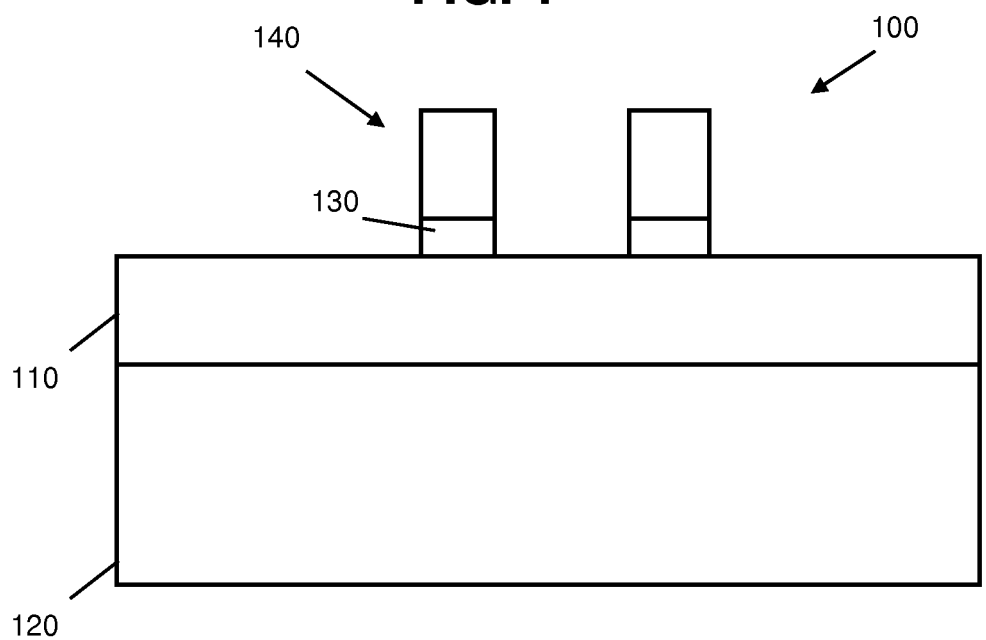
FIG. 2 illustrates a schematic representation of part of a substrate suitable for surface enhanced optical detection comprising a nanoring and metallic layer and an electrically insulating spacer limited to the area of the nanoring, according to an embodiment of the present invention.

The substrate 100 furthermore comprises a dielectric spacer 130 for spacing the electrically conductive layer 110 from the nanoparticles. The dielectric spacer 130 may be made of a dielectric material and can comprise e.g. silicon dioxide ($SiO_2$), polymers such as polystyrene, magnetic materials such as $Fe_2O_3$, or other magnetic oxides. The dielectric spacer 130 can be made of one material or can comprise several materials that can for instance be selected from the list above. Advantageously, the dielectric spacer 130 comprises (or consists of) $SiO_2$, silica having the additional advantage of being etchable. The thickness of the dielectric spacer 130 may be between 5 nm and 100 nm, e.g. between 10 nm and 50 nm. The dielectric spacer 130 may in some embodiments be based on a patterned electrically insulating layer. According to embodiments of the present invention, the dielectric spacer 130 typically only is present under the at least one nanoparticles, leaving the dielectric layer 110 uncovered by dielectric material at positions where no nanoparticles are present. The latter is advantageous as a larger integrated field enhancement can be obtained, due to the larger area of free electrically conductive surface being present. A schematic example of such a structure is illustrated in FIG. 2, indicating the dielectric spacer 130 being substantially only present under areas where the nanoparticle is present.

The substrate 100 furthermore comprises at least one nanoparticle 140, but advantageously a plurality of nanoparticles 140. The nanoparticles 140 may be monodisperse providing greater reproducibility, or have a broad size distribution providing wider resonances. In certain embodiments of the present invention, the nanoparticles 140 are not embedded. In other embodiments, a matrix linking the nanoparticles 140 together is present, so that a layer comprising nanoparticles 140 and a matrix is present on top of the dielectric spacer 130. The matrix can be any material able to act as a binder between the nanoparticles. Preferably, the matrix is a polymer matrix any polymer with binding properties to being suitable, although translucent or transparent polymers are preferred. The at least one nanoparticle 140 may be a plurality of nanoparticles 140 distributed over the surface of the substrate 100. They may be provided in a layer being a monolayer of nanoparticles 140. The nanoparticles 140 can be loosely packed or densely packed to form a monolayer with coverage on the substrate between 10% and 30%, or between 30% and 60% or between 60% and 80%, in the best case more than 80% and at most 90%. The coverage can be tuned from 10% to 80% or more (and up to 90%) by the concentration of the nanoparticles 140. At least part of the free space present between the nanoparticles is due to spatial limit, determined by the shape of the nanoparticles. The dielectric spacer 130 may also be functionalised for binding nanoparticles so that a close packing of nanoparticles 140 at the surface is obtained. Examples of adhesion (i.e. functionalisation) molecules comprise but are not limited to organosilanes, preferably organosilanes comprising a thiol or dithio function such as 3-mercaptopropyl-trimethoxysilane (MPTMS) or 3-mercapto-propyl-triethoxysilane (MPTES), among others. The functionalisation molecule may form a functionalisation layer on the substrate and may immobilize the nanoparticles on the substrate. A higher degree of coverage can also be obtained by using bimodal or very broad size distributions of the nanoparticles. In another embodiment of the present invention the nanoparticles are provided in a multilayer structure. Such multilayers can, for example, be built up layer by layer and may provide field confinement effects and optical field enhancement. The nanoparticles may be nanodisks, nanospheres, open nanoparticles, etc.

In some embodiments, open nanoparticles may be used, comprising an electrically conductive portion providing an opening to underlying material. Nanoparticles fulfilling this requirement may for example be nanorings or open nanospheres. In the following, these two examples will be described in more detail.

The at least one nanoparticle may for example be at least one nanoring, i.e. a ring-shaped or toroidal shaped nanoparticle. Such a nanoring may have a diameter in the range 60-1000 nm a ring width in the range 15-200 nm and a ring height in the range 10-100 nm. The shape of the nanoring is such that in the center an opening is provided in the electrically conductive portion to underlying material, e.g. to the underlying electrically insulating or electrically conductive layer. The electrically conductive portion may be made of a metallic material (such as gold (Au), silver (Ag), nickel (Ni), titanium (Ti), aluminum (Al), copper (Cu) or platinum (Pt) amongst others), a semi-metallic material, or a (preferably doped) semiconducting material (such as Si or GaAs amongst others) or any other conducting material used in the field. Preferred conductive materials are metals and doped semiconductors. More preferably, the conductive material is a metal. The electrically conductive portion can be made of a single conducting material or can comprise different conducting materials, for example selected from the list above. In some preferred embodiments, the electrically conductive portion of the nanoring comprises at least on material selected from the group consisting of Au, Ag and Al. Most preferably, the electrically conductive portion is made of gold.

The at least one nanoparticle also may be a nanodisc, supported by a dielectric nanodisc with smaller diameter.

Figure 3:
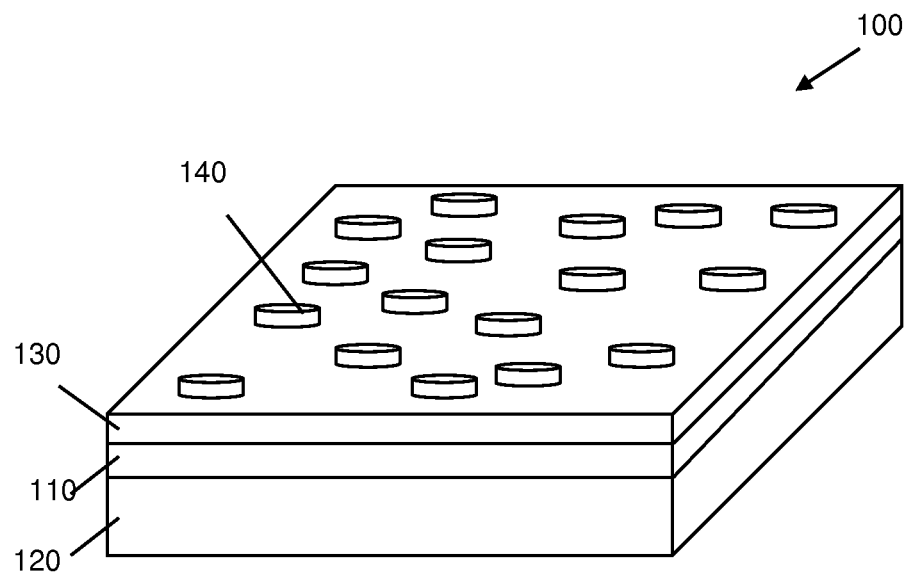
FIG. 3 illustrates a schematic representation of part of a substrate suitable for surface enhanced optical detection comprising a plurality of nanorings and metallic layer, according to an embodiment of the present invention.

By way of illustration, in FIG. 3 an example is shown of a substrate comprising an electrically conductive layer spaced from a plurality of nanorings, according to an embodiment of the present invention.

In some embodiments, the open nanoparticles are open shell nanoparticles. The open shell nanoparticles comprise an electrically conductive portion forming a conductive open shell, i.e. a conductive shell comprising an opening so that part of the underlying material is uncovered. They can have any shapes such as spheroidal or cuboidal. Preferably, they are substantially spherical. The electrically conductive portion (i.e. the shell) can be made of a metallic material (such as gold (Au), silver (Ag), nickel (Ni), titanium (Ti), aluminum (Al), copper (Cu) or platinum (Pt) amongst others), a semi-metallic material, or a (preferably doped) semiconducting material (such as Si or GaAs amongst others) or any other conducting material used in the field. Preferably, the core and the shell are made of different materials and the core is a dielectric and the shell a conductive material. The part of the core that is not covered with conducting material (i.e. the uncovered part) or in case of hollow nanoshells the part of the shell that is not present and through which the inside of the hollow nanoshell can be contacted, can be varied between 70% and 1% if a movable ion source is used in the etching process, with between 60% and 5% being preferred, between 50% and 5% being particularly preferred, between 45% and 5% being especially preferred, between 40% and 5% being particularly especially preferred, between 30% and 5% being even more preferred, between 20% and 5% being still more preferred, between 20% and 10% of the total surface area of the core being yet still more preferred. In embodiments, the surface area of the shell removed during the directional etching step is from 5 to 45% of the surface area of the shell. The open nanoshells may or may not have a dielectric core. The core is preferably made of a dielectric material and can comprise e.g. silicon dioxide ($SiO_2$) (e.g. the core particles used to make the nanoparticles can be silicon dioxide colloids), polymers such as polystyrene, magnetic materials such as $Fe_2O_3$, or other magnetic oxides. The core particles can be made of one material or can comprise several materials that can for instance be selected from the list above. When the core comprises more than one material, it is possible that it comprises both, conductive and dielectric materials if the outer surface of the core is dielectric. For instance, the core could be made of a conductive kernel coated with a dielectric coating. The important factor being that at least the outer surface of the core is a dielectric. Preferably, the core comprises (or consists of) $SiO_2$, silica having the additional advantage of being etchable. The shape of the core is preferably the same as the shape of the shell. Nanoshells of various core sizes are suitable. In an embodiment, the open nanoshells comprise a dielectric core partially surrounded by a conductive open shell. The size of the core particles (i.e. the core size) can be from 50 nm to 2000 nm, from 60 nm to 1500 nm, or from 80 nm to 1000 nm and preferably from 80 nm to 400 nm. The thickness of the conducting layer (i.e. the nanoshell layer) can be from 5 nm to 100 nm, from 7 nm to 50 nm or from 10 nm to 30 nm, or from 10 nm to 100 nm.

The open nanoshells may be oriented on the substrate in such a way that a majority, preferably 90% or more, most preferably substantially all of the open nanoshells have their opening directed away from the substrate (i.e. their opening do not touch the substrate, i.e. their opening is facing away from the substrate). In embodiments, if an arrow would be traced from the center of the particle to the center of the opening, this arrow would not point to the substrate and would preferably point away from the substrate. For instance, this arrow would make an angle of from 0 and 90° with the substrate, preferably 45 to 90°. In other words, said nanoparticles have the center of their shell open part at the half (or side) of the nanoparticles opposite to the half (or side) of said nanoparticle adjacent to said substrate.

Figure 4:
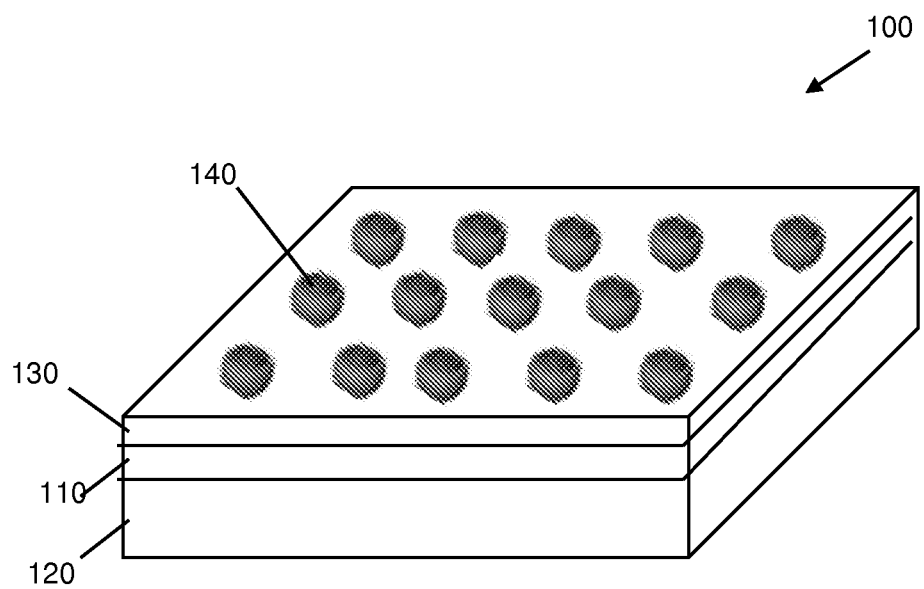
FIG. 4 illustrates a schematic representation of part of a substrate suitable for surface enhanced optical detection comprising a plurality of open nanoshells and metallic layer, according to an embodiment of the present invention.

FIG. 4 shows an example of an open shell nanoparticle on a substrate comprising an electrically conductive layer 110 spaced from the nanoparticles 140 by a dielectric layer 130. Substrates according to embodiments of the present invention with their open nanoshells layer (preferably monolayer) structures offer a stable and high density arrangement of open nanoshells on a substrate for various sensing application such as for instance surface-enhanced Raman scattering (SERS)-based biomolecules detection. In particular, nanoshells with a small core size (<100 nm) and a thin shell thickness (<10 nm)

having a relatively small particle size and having an optical response in near-infrared (NIR) region, are advantageously used in several applications, such as the biomedical imaging and thermotherapy for certain tumours. Although the examples of open nanoparticles are described in detail above, the present invention in some embodiments also relates to substrates comprising nanoparticles in the shape of disks or nanospheres.

It is an advantage of embodiments according to the present invention that the metal content of the substrate is high, resulting in an improved maximum and average electromagnetic field enhancement.

In one embodiment, tuning of the thickness of the spacer and the characteristics of the nanoparticles and/or the electrically conductive layer allows tuning the optical wavelength or optical wavelengths of operation of the substrate.

In another aspect of the present invention, according to some embodiments a substrate for surface enhanced optical detection wherein the substrate comprises an electrically conductive layer, a plurality of nanofeatures comprising an electrically conductive portion, and a dielectric spacer for spacing the electrically conductive layer from the nanofeatures. In some embodiments, the plurality of nanofeatures may be nanoholes or nanopores in an electrically conductive film. A possible implementation of such embodiments, i.e. wherein quadrupolar resonances for an enhanced electric field can be obtained, is a three layer structure, wherein the nanofeatures are implemented as a plurality of nanoholes or nanopores in an upper electrically conductive film. The structure further comprises, similar as the embodiments above, an electrically conductive lower layer and a dielectric spacer layer. The electrically conductive lower layer may be any electrically conductive layer as described above, such as for example a continuous metal (e.g. Au) film. The dielectric spacer may be any type of dielectric layer as described above, such as for example a continuous dielectric film (e.g. SiO2). The nanofeatures may be provided as nanopores or nanoholes in an upper electrically conductive layer. For example, the upper electrically conductive layer may be a thin layer, e.g. having a thickness in the range 20 nm to 50 nm. It may be made of any suitable electrically conductive material, such as for example of a metal like Au. The nanofeatures may be provided as nanopores or nanoholes perforated in the electrically conductive upper layer. In some embodiments, the nanoholes advantageously may have a diameter of 50-200 nm. One example of a manufacturing method for nanoholes may be as described by Prikulis in NanoLetters (4) 2004 pages 1003-1007.

In operation, in the upper electrically conductive layer perforated with holes, the light excites surface plasmons in the metal film, giving rise to a resonance in the holes (and a subsequent enhancement of the electric field). The excitation of the "hole resonance" will give rise to image charges in the lower electrically conductive layer, resulting in a quadrupolar excitation with a reduced linewidth and exhibiting larger field enhancements. Moreover, tuning the thickness of the upper electrically conductive layer and/or of the dielectric spacer will allow to tune the resonance wavelength. It is an advantage of embodiments according to the present invention with respect to surface enhanced Raman scattering that a large amount of metal is covering the surface.

Figure 14A:
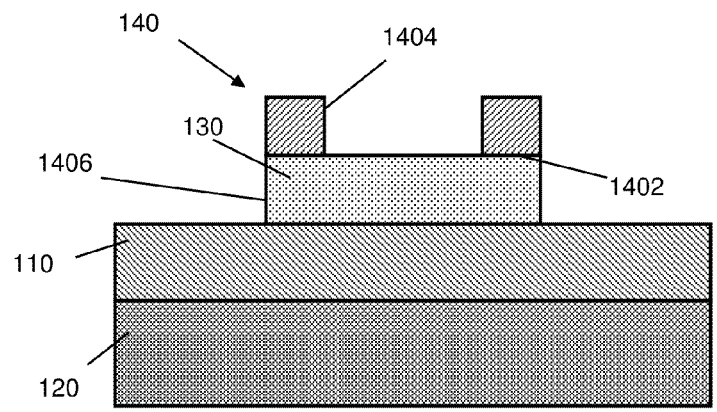
FIG. 14a to FIG. 14c illustrates a number of substrates comprising a nanoparticle with a dielectric spacer under the nanoparticle according to embodiments of the present invention.
Figure 14B:
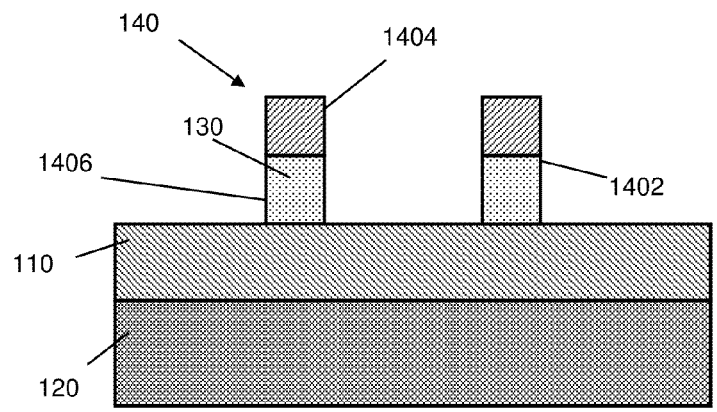
Figure 14C:
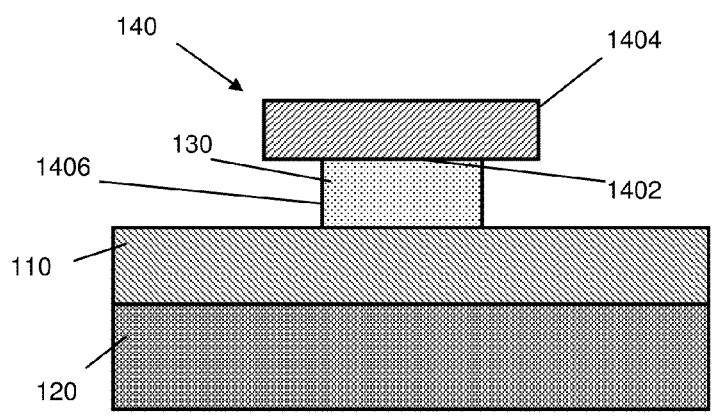

According to embodiments of the present invention, the at least one nanoparticle and the dielectric spacer may be arranged such that the at least one nanoparticle and the dielectric spacer are interfaced along a first major surface. Such a first major surface may be parallel with the average plane through the substrate. The first major surface 1402 is indicated for different embodiments of the present invention illustrated in FIG. 14a to FIG. 14c. In a similar manner, the upstanding surface of the nanoparticle 1404 and the upstanding surface of the dielectric spacer 1406 also are illustrated in FIG. 14a to FIG. 14c. According to embodiments of the present invention the upstanding surface and the first major surface make an angle of at least 45° with respect to each other. According to embodiments of the present invention, the at least one nanoparticle and the dielectric spacer are interfaced along the first major surface and the at least one nanoparticle comprises an upstanding surface that is not in line with an upstanding surface of the dielectric spacer. The latter results in the advantage that at the inner side of the nanoparticle or at an inner corner of a structure formed by the nanoparticle and the dielectric spacer, spots of high electric field, e.g. also referred to as hot spots, can be present during use, resulting in good electric field enhancement.

By way of illustration, embodiments of the present invention not being limited thereto, a number of examples based on nanorings and nanodiscs are shown wherein the at least one nanoparticle and the dielectric spacer fulfill the above mentioned condition. It will be clear that starting from the examples shown in FIG. 14a to FIG. 14c, the person skilled in the art will without inventive skills derive alternative embodiments, such as for example based on nanoparticles being open nanoshells.

In FIG. 14a a first example is shown wherein the at least one nanoparticle is a nanoring 140 and the dielectric spacer 130 is a nanodisc. Furthermore also the electrically conductive layer 110, the major surface 1402 and the upstanding surfaces 1404 and 1406 are shown.

In FIG. 14b a second example is shown wherein the at least one nanoparticle is a nanoring 140 and the dielectric spacer 130 also is a ring, having the same inner and outer diameter. Alternatively, the inner diameter of the dielectric spacer 130 also could be selected to be different. Furthermore, also the electrically conductive layer 110, the major surface 1402 and the upstanding surfaces 1404 and 1406 are shown.

In FIG. 14c a third example is shown, wherein the at least one nanoparticle is a nanodisc 140 having a predetermined diameter and wherein the dielectric spacer 130 is a nanodisc having a smaller diameter. The latter can for example be obtained by underetchning, the method of manufacturing not being limited thereto. Again, the electrically conductive layer 110, the major surface 1402 and the upstanding surfaces 1404 and 1406 are shown.

Figure 15A:
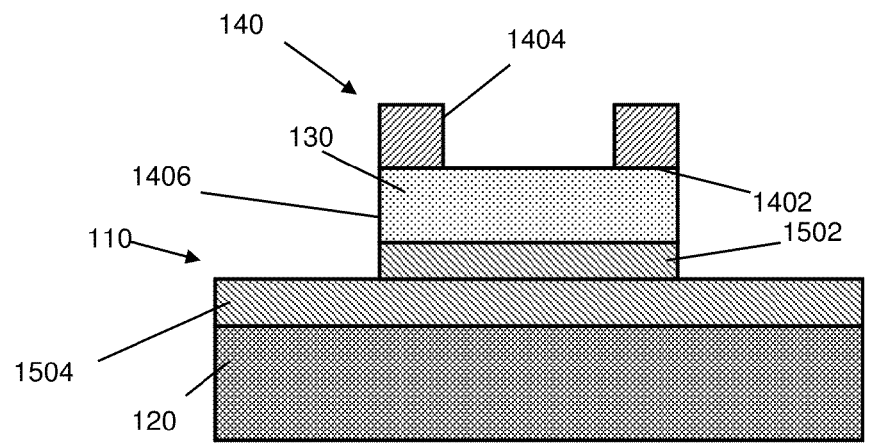
FIG. 15a to FIG. 15d illustrates a number of substrates comprising a nanoparticle with a dielectric spacer under the nanoparticle and a partially patterned electrically conducting layer according to embodiments of the present invention.
Figure 15B:
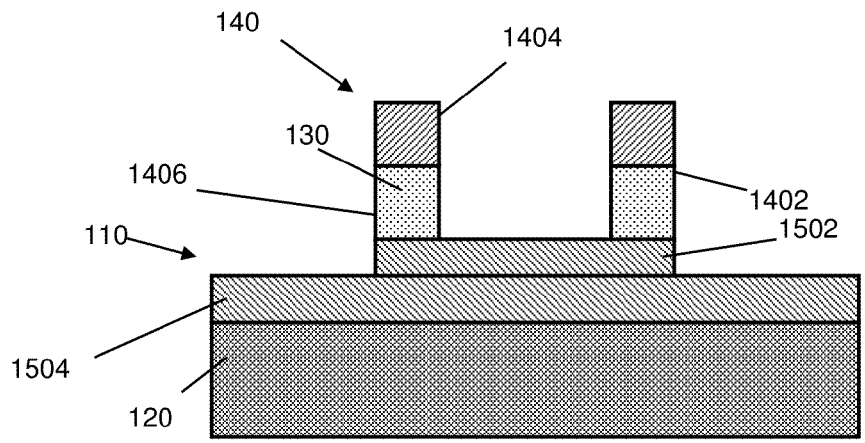
Figure 15C:
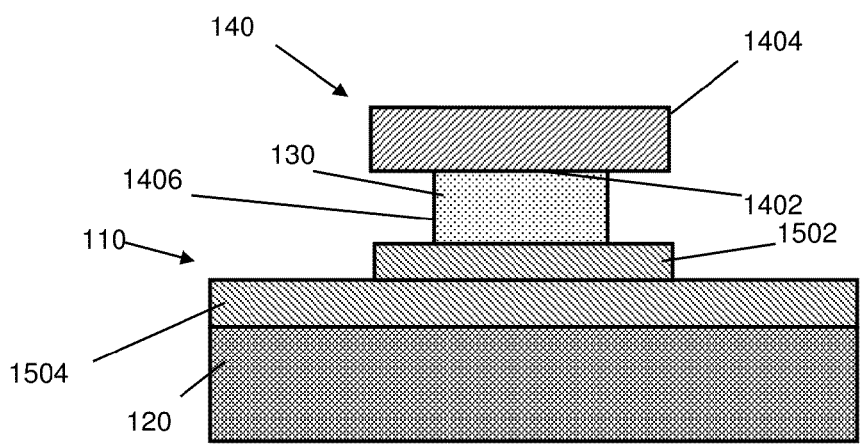
Figure 15D:
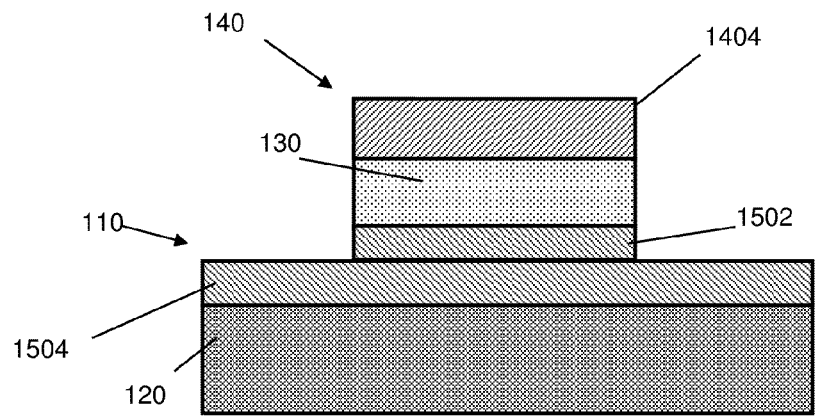

In a further aspect of the present invention, embodiments disclose substrates as described in the first aspect, whereby the underlying electrically conducting layer 110 is partially patterned. With partially patterned there is meant that the layer has an upper part 1502 and a bottom part 1504, whereby the upper part 1502 is patterned such that the electrically conducting layer 110 is present only under the dielectric spacer, whereas the bottom part 1504 forms a continuous layer. The latter is illustrated for a number of examples in FIG. 15a to FIG. 15d. FIG. 15a illustrates the example wherein a nanoparticle 140 nanoring is stacked on a nanodisc shaped dielectric spacer 130 which is itself stacked on a nanodisc shaped electrically conducting portion in the upper part 1502 of the electrically conducting layer. In FIG. 15b, a substrate 100 is shown wherein the nanoparticle 140 is a nanoring positioned on a nanoring shaped dielectric spacer 130 and whereby the dielectric spacer 130 is positioned on a nanodisc shaped electrically conducting portion in the upper part 1502 of the electrically conducting layer. In FIG. 15c, a substrate 100 is shown wherein the nanoparticle 140 is a nanodisc positioned on a dielectric spacer 130 nanodisc, whereby the diameter of the dielectric spacer 130 nanodisc is smaller than the nanoparticle 140 nanodisc. The dielectric spacer 130 is supported by an electrically conducting nanodisc in the upper part of the electrically conductive layer 1502. In FIG. 15d, an example is shown of a stack of nanodiscs having substantially the same diameter, the stack of nanodiscs comprising a nanoparticle 140 nanodisc, supported by a dielectric spacer 130 nanodisc, at its turn supported by an electrically conductive nanodisc being part of the upper portion 1502 of the electrically conductive layer. In all examples, the bottom portion 1504 of the electrically conducting layer also is shown, which is a continuous film.

Partially patterning of the electrically conducting layer 110 is advantageous as it allows spatially even better defining the plasmonic mode, resulting in larger field enhancements. It is an advantage of embodiments according to the present invention that the sensitive parts of the substrates can be reached by the sample. Furthermore, it also is advantageous that the plasmonic mode does not or less leak to the metal film, thus limiting the losses.

Partially patterning of the electrically conducting layer 110 also has the advantage that the number of hot spots can be increased, e.g. doubled. Large field enhancements will occur on the top disk as well as on the bottom structure.

Figure 16:
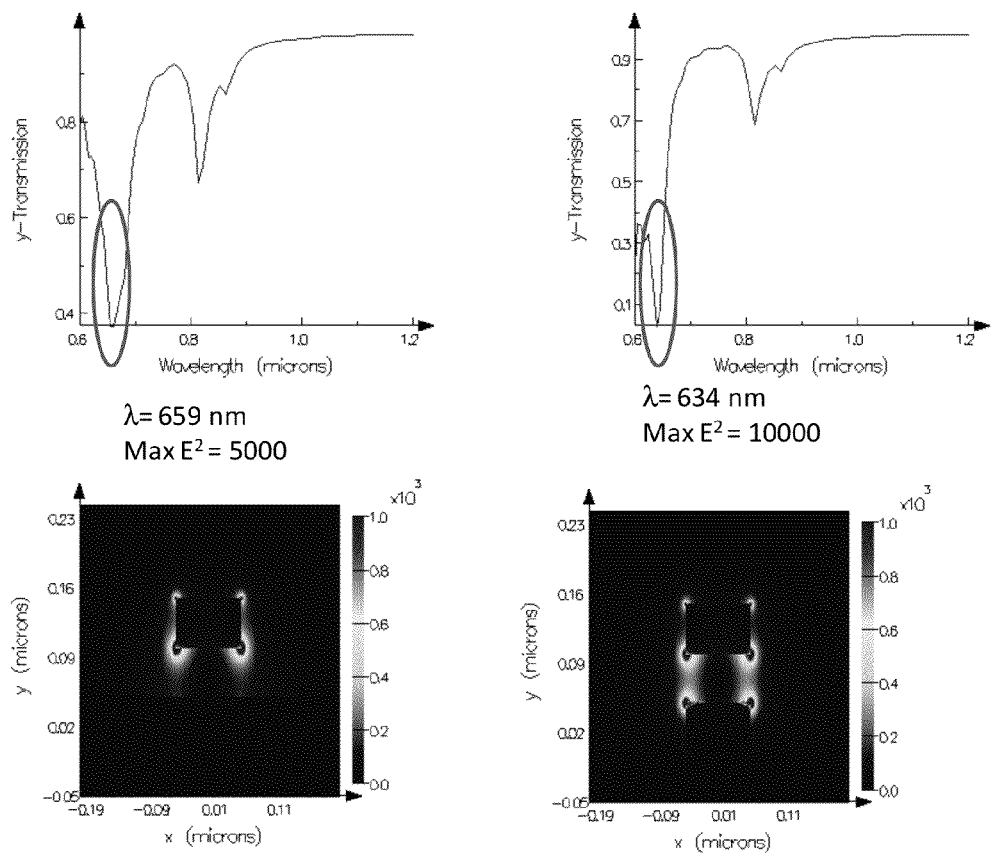
FIG. 16 illustrates a finite difference time domain calculation of a plasmonic mode in a substrate as shown in FIG. 15d, illustrating advantages of embodiments according to the present invention.

By way of illustration, embodiments of the present invention not being limited thereby, Finite Difference Time Domain simulations have been performed on both a substrate with a partially patterned electrically conducting layer 110, the present example corresponding with the substrate shown in FIG. 15d and results being shown on the right hand side of FIG. 16, and on a substrate with a conventional electrically conducting layer, i.e. not partially patterned, results being shown on the left hand side of FIG. 16. It can be seen that the number of hot spots is increased as not only at the interface between the nanoparticle and the dielectric spacer hot spots are formed but also at the interface between the dielectric spacer and the upper part of the partially patterned electrically conducting layer. The largest field intensity is at the corners or edges of the nanoparticles, outside the nanoparticles.

Embodiments of the present aspect may make use of open nanoparticles, disc shaped nanoparticles, nanorings, . . . .

In another aspect, the present invention relates to a method for manufacturing a substrate suitable for surface enhanced optical detection. The method may be especially suitable for manufacturing a substrate as described in the first aspect of the present invention, although embodiments of the present invention are not limited thereto. The method according to embodiments of the present invention comprising obtaining a supporting substrate. Such a supporting substrate may have the properties as set out in the first aspect. The method also comprises providing an electrically conductive layer on the supporting substrate. The electrically conductive layer may have the properties as set out in the first aspect. The latter may be performed in any suitable manner, e.g. using physical deposition techniques such as for example physical vapour deposition such as sputtering, thermal evaporation, ebeam evaporation, chemical deposition techniques such as for example chemical vapour deposition, molecular beam epitaxy, etc. The method also comprises providing a dielectric spacer layer on the electrically conductive layer. The dielectric spacer layer may have the properties as set out in embodiments of the first aspect. It may be provided using conventional deposition techniques, such as for example using physical deposition techniques such as for example physical vapour deposition, chemical deposition techniques such as for example chemical vapour deposition, spin coating etc.

In a subsequent step, the method of manufacturing comprises providing at least one nanoparticle on the dielectric spacer layer. The at least one nanoparticle may have the properties as set out in embodiments of the first aspect. In some embodiments, the nanoparticles may be open nanoparticles. Open nanoparticles thereby are nanoparticles comprising an electrically conductive portion wherein the electrically conductive portion providing an opening to an underlying material. Examples thereof are nanorings and open nanospheres.

In one exemplary embodiment nanorings can be directly grown on the dielectric spacing layer. In another exemplary embodiment, open nanospheres can be provided by first making and providing a nanosphere solution on the electrically insulating spacer layer and thereafter directional removing of part of the nanosphere. By way of illustration, an example of how this can be achieved is described below, embodiments of the present invention not being limited thereby.

First, nanoparticles comprising a dielectric core and a conductive shell can be prepared. Starting with dielectric core particles, a conductive layer can be deposited thereon. Deposition of the conducting layer can for example be done by seeding followed by electroless plating, or polymerization, or other chemical techniques. The surface roughness of the shells is mainly determined by the deposition technique used (e.g. the seeding and electroless plating process) to put the conducting layer on the core. That way, dielectric nanoparticles covered with a conducting layer can be prepared. Dimensions of open-nanoshells can be controlled by tuning core sizes and shell thicknesses in a broad range. The method may comprise the steps of providing a layer as described in the first aspect on a substrate. Before deposition, the substrate can be treated, for example by cleaning with deionised water, piranha solution, UV ozone treatment, ultrasonication or any other method known in the art. In embodiments, prior to provide said layer on said substrate, the substrate may be chemically functionalised. Functionalisation can for instance be performed by applying an organosilane layer on the substrate surface. Deposition of the nanoshell layer can be done by drop-casting of nanoshells suspension, spin coating of nanoshells suspension, immersing functionalized substrate into nanoshells suspension, creating ordered monolayers, self-assembly, or other techniques well known to the person skilled in the art. The layer comprises or consists of nanoshell particles. Providing the layer on the substrate result in the forming of a layer of nanoshell particles on the substrate. In this aspect of the present invention, the nanoshell particles of the provided layer comprise a dielectric core and a conductive shell. In embodiments, the method according to the second aspect of the present invention comprises the step of depositing a layer on a substrate, said layer comprising nanoparticles, thereby forming a layer of nanoparticles on said substrate wherein said nanoparticles comprise a dielectric core and a conductive shell. Once the layer is provided on the substrate, part of the conductive shell, not in contact with the substrate surface, is removed. Preferably, part of the conductive shell is removed at the side of said nanoparticles opposite to the side of the nanoparticles adjacent to the substrate, thereby forming nanoparticles comprising a conductive open shell. In embodiments, the step of removing part of the conductive shell may be performed via a directional removing (e.g. directional etching technique) such as e.g. ion milling. Directional removing (e.g. etching) is advantageous as this allows removing (e.g. etching) the material at a place away from the substrate (e.g. only at the top side of the particles) thereby creating a layer of open nanoshells on the substrate, whereby at least 50% of the open nanoshells, preferably at least 90% of the open nanoshells, most preferably substantially all open nanoshells have substantially the same orientation. So, in embodiments, most or all open-nanoshells are "facing up" with the open part at the side opposite to the substrate. That way, open nanoshells layer (e.g. a monolayer thereof) structures can be obtained on the substrate. The etching rate is material dependent, and depends on the etching technique, the system that is used and the operating conditions of the system.

Instead of ion milling, other techniques such as chemically assisted ion beam etching (CAIBE), reactive ion etching (RIE), or others with similar directional etching behaviour, can be used. That way an etch chemistry can be chosen that etches the conducting material much faster than the dielectric core, such that the conducting material can be etched highly selectively with respect to the dielectric core, thereby etching the conducting material while leaving the core unetched. An alternative directional removing technique suitable when the layer of nanoparticles is embedded in a matrix (e.g. a polymer matrix), is to mechanically remove (e.g. via scrubbing in a Chemical Mechanical Polishing) (CMP)-like process) an upper layer of the layer until the dielectric core of the particles is reached. This results in polymer layer comprising metallic spots or rings at its surface.

In some embodiments, once part of the conductive open shell is removed, the method may further comprise a step of removing the dielectric core from the open shell nanoparticles. This results in a layer of hollow open nanoshells. The chemistry used for removing the core should preferably be chosen such that it can selectively remove the core without affecting much the conducting shell. Preferably, the chemistry used for removing the core should only remove the core and leave the open conducting shell intact. In the case of Au open-nanoshells with silica core for example, removing the silica core can be done by using aqueous HF for suspensions or vapor-phase HF for Au open-nanoshells monolayer structures. This keeps the Au open-nanoshells intact.

Whereas in the above description the example is provided of manufacturing of open nanoparticles, embodiments of the present invention are not limited thereto.

Methods according to embodiments of the present invention allow good control of the nanoparticles, e.g. in some embodiments of the reduced-symmetrical geometry of the nanoparticles, and allow monolayer structures to be realised with upward-oriented aperture on a substrate with good control and reproducibility. This makes the fabricated nanorings, open nanoshells (e.g. Au open nanoshells) and substrate having a mono(layers) thereof suitable for a range of applications, for example, as active components in thermotherapy system and SPR biosensors. In particular, these particles with the features of nanoaperture optionally comprising nanotip structures can be good substrates for optical spectroscopy techniques such as surface-enhanced Raman scattering (SERS)-based molecule detection, or surface-enhanced resonance Raman scattering (SERRS), surface-enhanced coherent anti-Stokes Raman scattering (SECARS), surface-enhanced infrared absorption (SEIRA), surface-enhanced fluorescence, surface-enhanced hyper-Raman scattering (SE-HRS). According to embodiments of the present invention, the method of manufacturing also comprises removing the dielectric spacer layer at those positions where the dielectric spacer is not positioned under the at least one open nanoparticle. In the case of a nanoring, this includes positions outside the nanoring as well as at the center of the nanoring. The latter results in more free metal surface, such that electromagnetic field enhancement again can be increased. Such removal may be performed using etching. In some embodiment wet etching or dry etching can be used. For example for $SiO_2$ an HF etch (wet) can be used, an HF vapour etch (gas phase) can be used, a CF4 reactive ion etching can be used, an SF6 reactive ion etching can be used, . . . .

Furthermore, the dielectric spacer and the at least one nanoparticle may be configured such that the at least one nanoparticle and the dielectric spacer are interfaced along a first major surface and the at least one nanoparticle comprises an upstanding surface not in line with an upstanding surface of the dielectric spacer. Furthermore, the method may comprise partially patterning the electrically conductive layer for generating a top portion of the electrically conductive layer that is only present locally under the dielectric spacer and a bottom portion of the electrically conductive layer being a continuous film.

In one aspect, the present invention also relates to the use of a substrate as described in an embodiment of the first aspect or as obtained using a method according to an embodiment of the second aspect. The use of such a substrate may be for surface enhanced resonance spectroscopy, but also for other optical techniques such as for example surface-enhanced resonance Raman scattering (SERRS), surface-enhanced coherent anti-Stokes Raman scattering (SECARS), surface-enhanced infrared absorption (SEIRA), surface-enhanced fluorescence, surface-enhanced hyper-Raman scattering (SE-HRS), refractive index sensing.

Figure 5:
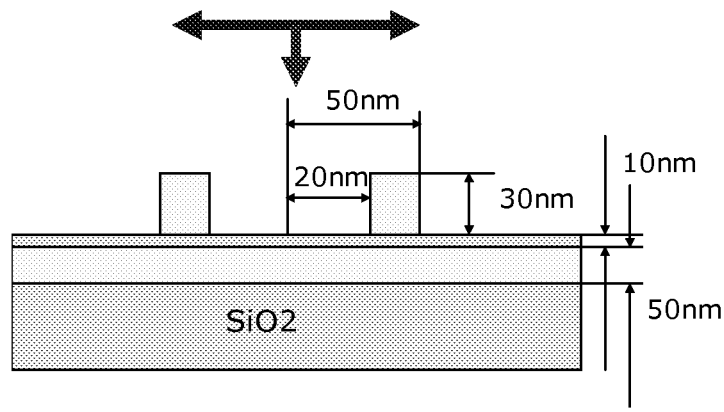
FIG. 5 illustrates a schematic representation of part of a substrate suitable for surface enhanced optical detection comprising a nanoring, a metallic layer and a ring shaped dielectric layer for spacing, according to an embodiment of the present invention.

By way of illustration, embodiments of the present invention not being limited hereto, simulation results are shown for an exemplary SERS substrate as depicted in FIG. 5. The exemplary SERS substrate according to an embodiment of the present invention comprises a gold (AU) metal ring on a dielectric spacer, in the present example being a $SiO_2$ layer, spacing the nanoring from a metal layer, in the present example being a gold layer, the gold layer being deposited on a $SiO_2$ substrate. The SERS substrate according to the present example is shown by way of illustration in FIG. 5. In the present example, embodiments of the present invention not being limited thereto, the dimensions of the different components were as follows. The gold nanoring had a diameter of 50 nm and a ring width of 30 nm. The height of the nanoring was 30 nm. The dielectric spacer layer according to the present example had a thickness of 10 nm. The gold layer had a thickness of 50 nm.

Figure 6:
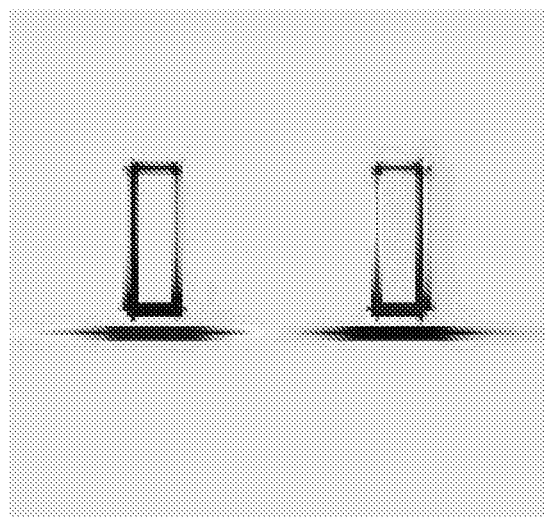
FIG. 6 illustrates a charge plot indicating a quadrupolar charge distribution in the ring/metal film structure of a substrate according to an embodiment of the present invention.
Figure 7:
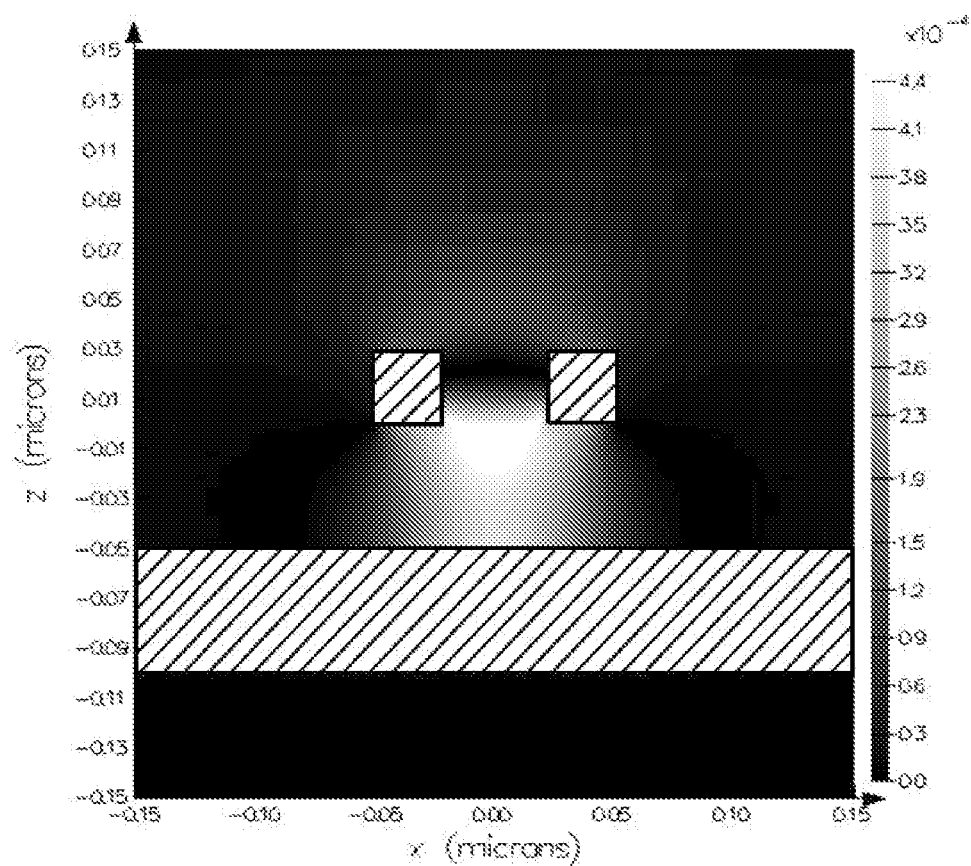
FIG. 7 illustrates a magnetic field $H_y$ profile indicating a magnetic resonance in a substrate according to an embodiment of the present invention.
Figure 8:
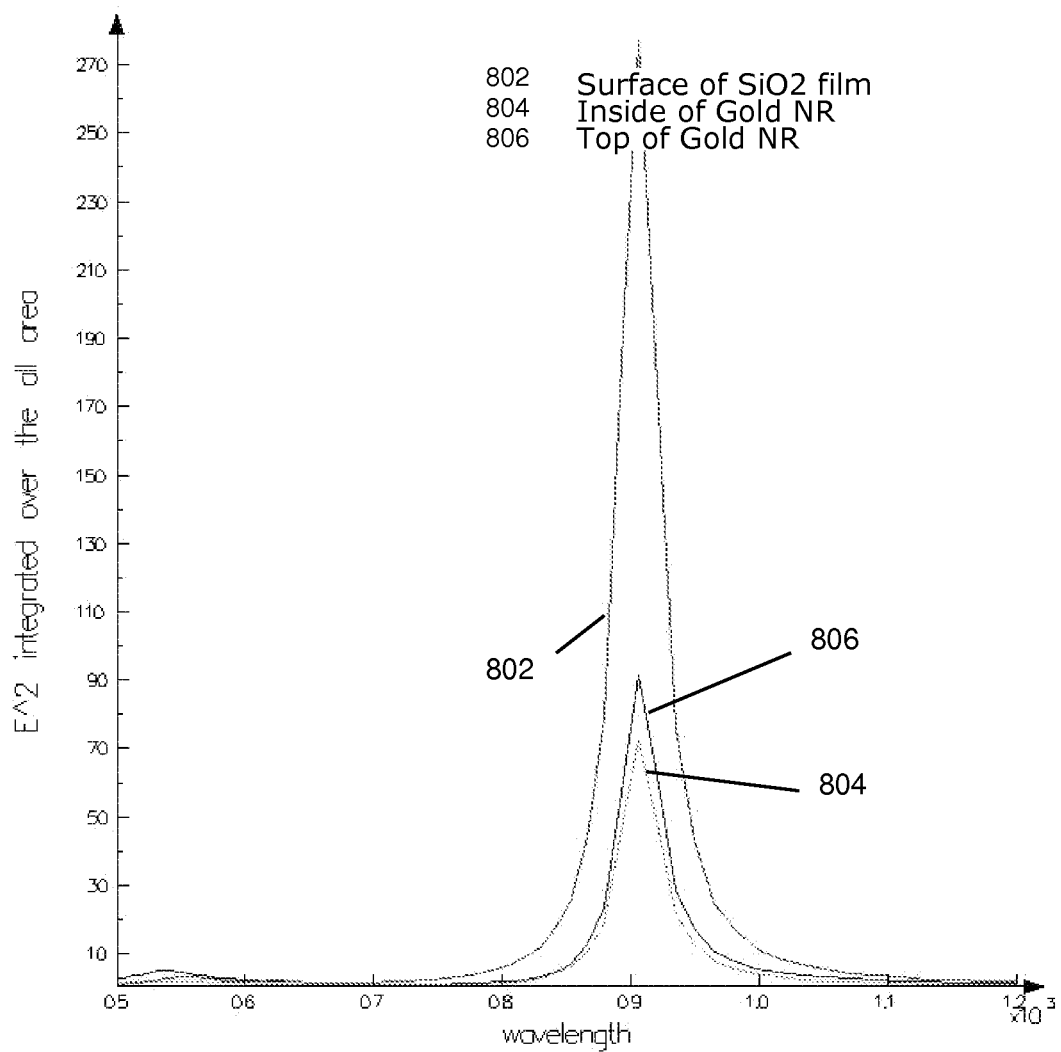
FIG. 8 illustrates the integrated field enhancement near the ring/metal film heterostructure, as can be obtained in an embodiment of the present invention.
Figure 9:
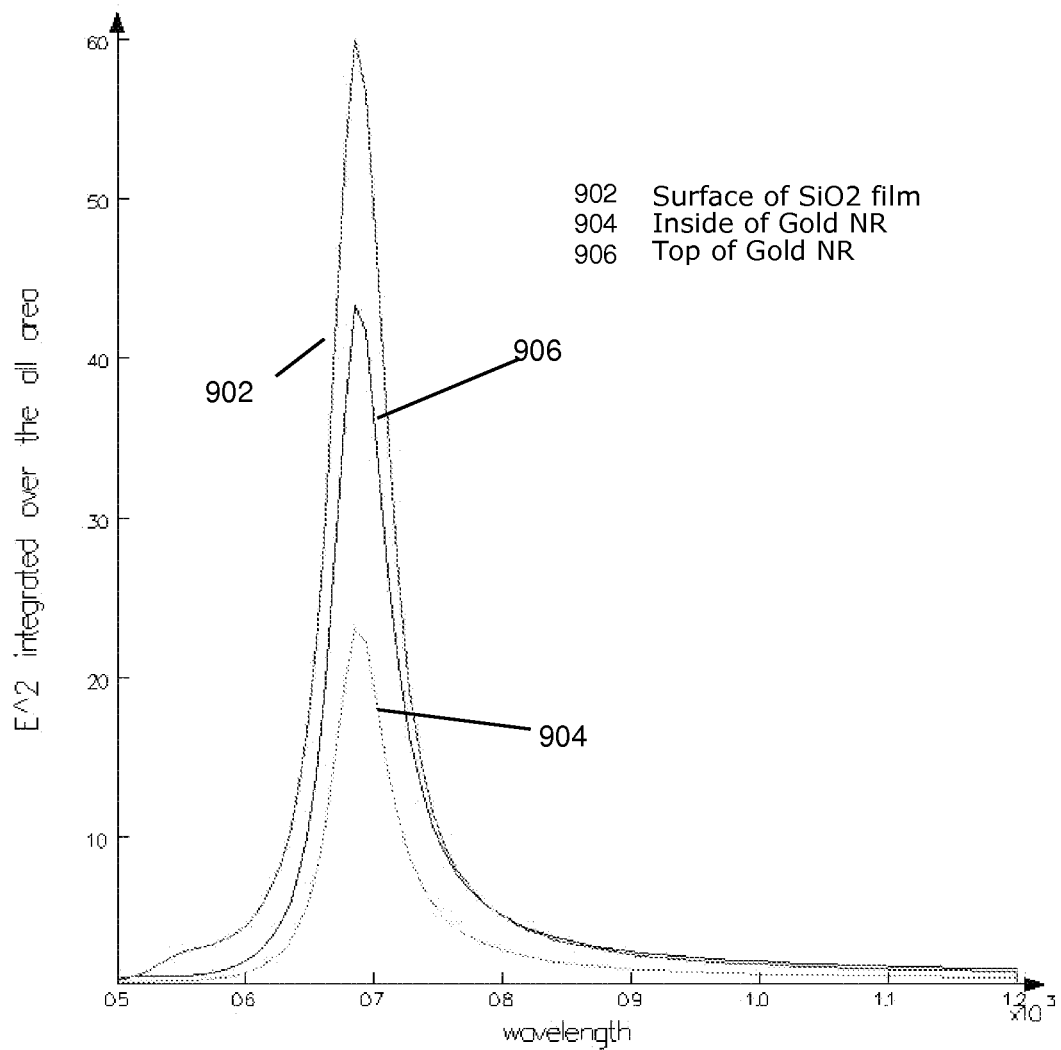
FIG. 9 illustrates the integrated field enhancement near the dielectric layer/nanoring structure, as can be obtained in an embodiment of the present invention.

It has surprisingly been found that as radiation excites a dipolar resonance in the nanoring, image charges are created in the metal film, which generate a quadrupolar resonance. The excitation of the resonance results in a significant reduction of radiative scattering of the nanostructure. By doing so, a higher quality factor and a better confinement of optical energy in the nanostructure can be obtained. In combination with a thin dielectric layer, this allows generating a large electric field, e.g. far larger than is the case for single rings. FIG. 6 illustrates a charge plot indicating a quadrupolar charge distribution the nanoring and electrically conductive layer. In FIG. 7, the magnetic field $H_y$ profile for the structure is indicated. This magnetic field profile indicates the occurrence of a magnetic resonance in the system. In FIG. 8 and FIG. 9 an integrated field enhancement is shown respectively near the nanoring/electrically conductive film heterostructure and near the dielectric layer and the nanoring structure in the absence of an electrically conductive film. The integrated field enhancement is shown at the surfaced of the dielectric spacer 802/902, inside the nanoring 804/904 and at the top of the nanoring 806/906. It can be seen that the obtained improvement is about a factor 4.5.

Further by way of illustration, comparative results are shown for a structure based on nanorings wherein a full dielectric spacer layer is provided and a structure based on nanorings wherein the dielectric spacer is provided as a dielectric nanoring underlying the metal nanoring. The structure with full dielectric spacer is shown in FIG. 10a whereas the structure with nanoring shaped dielectric spacer is shown in FIG. 10b.

Figure 10A:
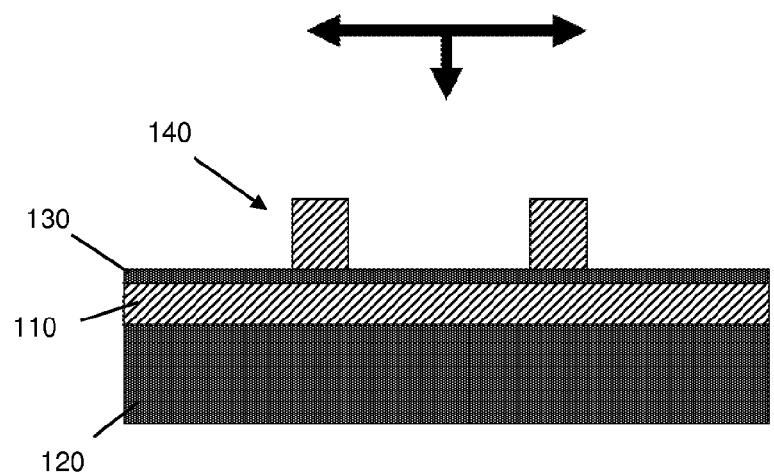
FIG. 10a and FIG. 10b illustrate an exemplary substrate according to an embodiment of the present invention based on a metal nanoring and a full layer dielectric spacer and nanoring dielectric spacer respectively.
Figure 10B:
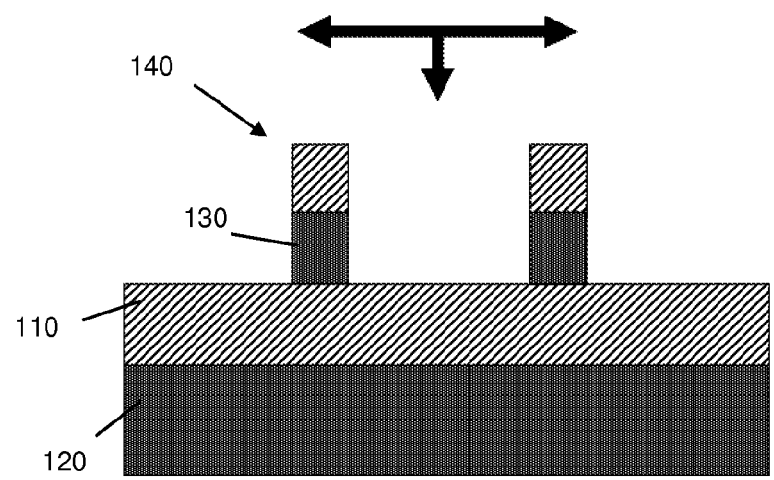
Figure 10C:
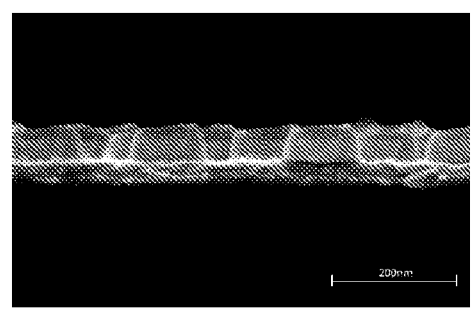
FIG. 10c illustrates a scanning electron microscopy image of a metal nanoring/dielectric nanoring structure, according to an embodiment of the present invention.
Figure 11:
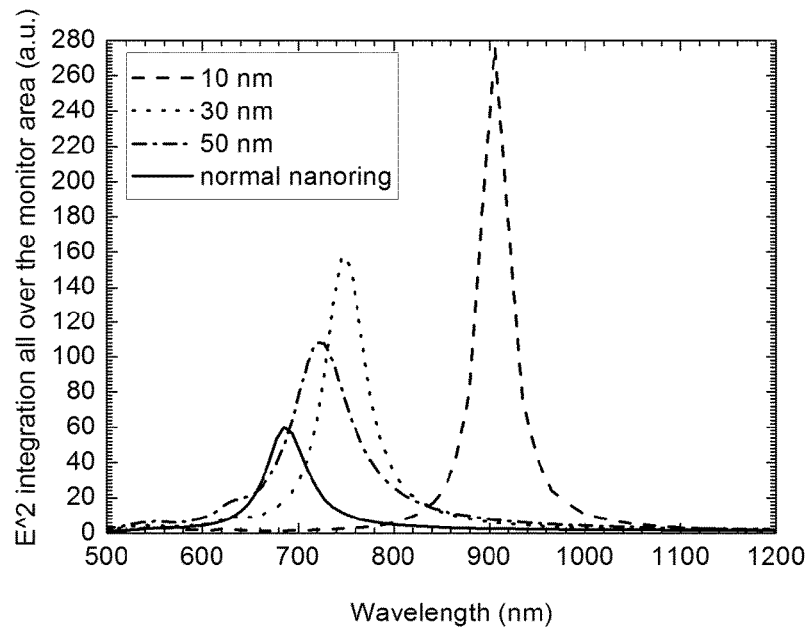
FIG. 11 illustrates the integrated electric field strength at the surface of the dielectric spacer for a reference and a plurality of substrates according to embodiments of the present invention.

FIG. 10c illustrates, by way of example, a scanning electron microscopy image of a substrate wherein both a metal nanoring and a dielectric spacer nanoring is present in agreement with the schematic illustration shown in FIG. 10b. The results shown are based on a $SiO_2$ dielectric spacer, a lower electrically conductive layer being a gold metal layer, and gold nanorings. The integrated electric field strength at the surface of the dielectric spacer, in the present example being $SiO_2$, is shown in FIG. 11 for a plurality of situations, i.e. for nanorings whereby no lower electrically conductive layer is present (i.e. for a normal nanoring), for a 10 nm thick dielectric spacer between the nanorings and the lower electrically conductive layer, for a 30 nm thick dielectric spacer between the nanorings and the lower electrically conductive layer and for a 50 nm thick dielectric spacer between the nanorings and the lower electrically conductive layer.

Figure 12:
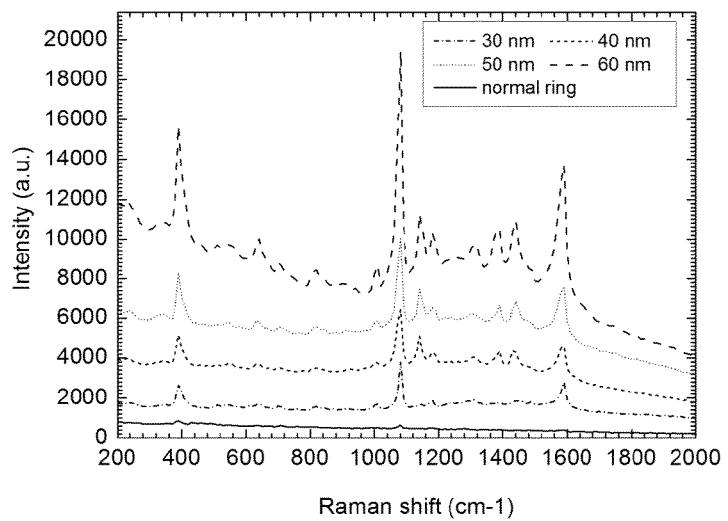
FIG. 12 illustrates SERS data obtained for a monolayer of 4-ATP on gold rings, as can be obtained using an embodiment of the present invention.

FIG. 12 illustrates SERS data obtained for a monolayer of 4-ATP on gold rings, for a plurality of different situations, i.e. for nanorings whereby no lower electrically conductive layer is present (i.e. for a normal nanoring) and for a 30 nm, 40 nm, 50 nm and 60 nm thick spacer between the nanorings and the lower electrically conductive layer.

Figure 13A:
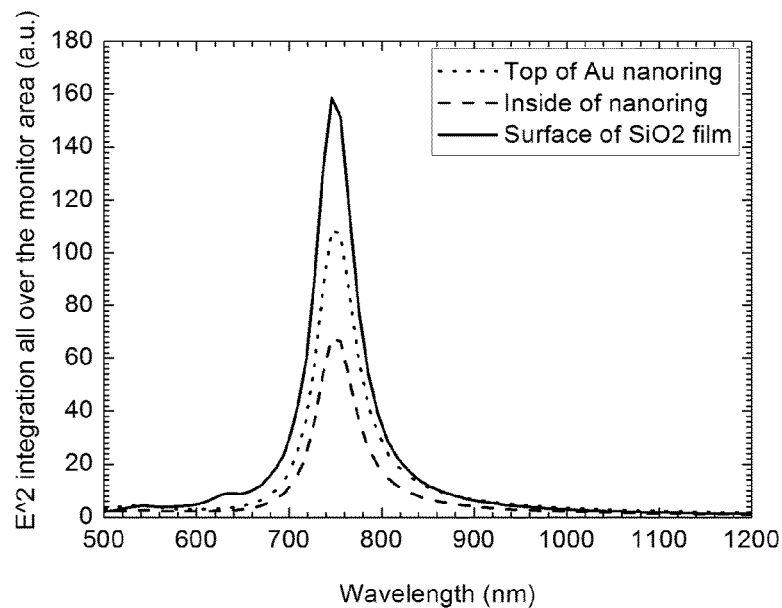
FIG. 13a and FIG. 13b illustrate the integrated electric field strength as function of the wavelength at a number of different positions for the structure in FIG. 10a and FIG. 10b.
Figure 13B:
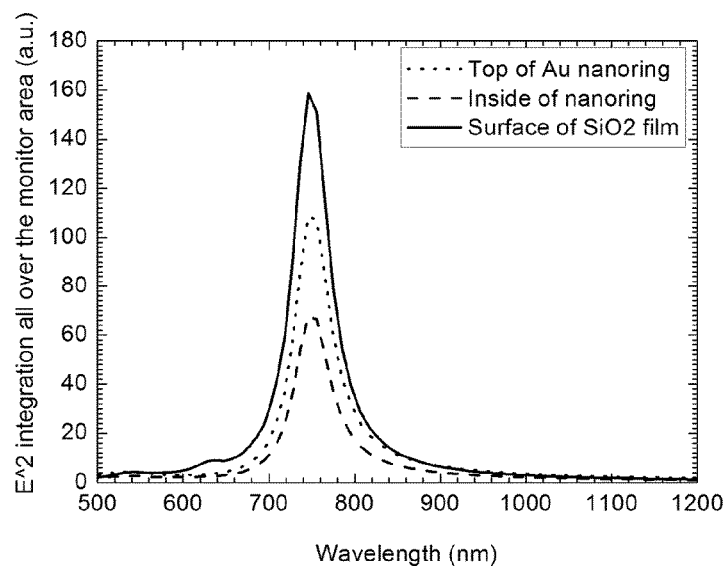

FIG. 13a and FIG. 13b illustrate the integrated electric field strength as function of the wavelength at a number of different positions for the structure in FIG. 10a and FIG. 10b respectively. FIG. 13a illustrates the integrated electric field strength for a structure with full dielectric spacer layer in a plane just above the nanoring, in a horizontal plane through the centre of the nanoring, in a plane near the $SiO_2$ surface. FIG. 13b illustrates the integrated electric field strength for a structure with dielectric spacer nanorings in a plane just above the nanoring, in a plane between the electrically conductive nanoring and the dielectric spacer nanoring and on the surface of the lower electrically conductive layer.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A substrate for surface enhanced optical detection, the substrate comprising:
    an electrically conductive layer;
    at least one nanoparticle comprising an electrically conductive portion; and
    a dielectric spacer for spacing the electrically conductive layer from the at least one nanoparticle,
    wherein the dielectric spacer is a dielectric material substantially only present under the at least one nanoparticle, leaving the electrically conductive layer uncovered from dielectric material at positions away from the at least one nanoparticle,
    wherein the at least one nanoparticle and the dielectric spacer are interfaced along a first major surface and wherein the at least one nanoparticle comprises an upstanding surface not in line with an upstanding surface of the dielectric spacer, and
    wherein the electrically conductive layer is partially patterned, such that the electrically conductive layer comprises a to part that is only locally present under the dielectric spacer and a bottom part that is a continuous film.

2. A substrate according to claim 1, wherein the at least one nanoparticle is at least one nanoring.

3. A substrate according to claim 2, wherein the dielectric spacer is a dielectric nanoring positioned under the at least one nanoparticle.

4. A substrate according to claim 1, wherein the at least one nanoparticle is a nanodisc.

5. A substrate according to claim 1, wherein the dielectric spacer is a dielectric disc positioned under the at least one nanoparticle.

6. A substrate according to claim 1 wherein a diameter of the dielectric spacer is configured for leaving a bottom side of the at least one nanoparticle facing the electrically conductive layer partially uncovered.

7. A substrate according to claim 1, wherein the at least one nanoparticle, dielectric spacer and electrically conductive layer are arranged for having a quadrupolar charge distribution in the substrate.

8. A substrate according to claim 1, wherein the substrate is integrated in a sensing device for sensing based on surface enhanced optical detection.

9. A substrate according to claim 8, wherein the sensing device is configured to sense glucose.

10. A substrate according to claim 1, wherein the electrically conductive layer is selected from the group consisting of a gold layer, a silver layer, and an aluminum layer.

11. A method for manufacturing a substrate suitable for surface enhanced optical detection, the method comprising
    obtaining a supporting substrate;
    providing an electrically conductive layer on the supporting substrate;
    providing a dielectric spacer layer on the electrically conductive layer
    providing at least one nanoparticle tl-4G1 on the dielectric spacer layer;
    removing the dielectric spacer layer at these positions where the dielectric spacer material is not positioned under the at least one nanoparticle such that the at least one nanoparticle and the dielectric spacer are interfaced along a first major surface and the nanoparticle comprises an upstanding surface not in line with an upstanding surface of the dielectric spacer; and
    partially patterning the electrically conductive layer for generating a to portion of the electrically conductive layer being only locally present under the dielectric spacer and a bottom portion of the electrically conductive layer being a continuous film.

12. A method for manufacturing a substrate according to claim 11,
  wherein removing the dielectric spacer material comprises etching the dielectric spacer material at the positions where the dielectric spacer is not positioned under the at least one nanoparticle.

* * * * *